Dec. 27, 1927.

Re. 16,836

H. S. COOK

HYPODERMIC SYRINGE

Original Filed Oct. 21, 1916

Harry S. Cook Inventor

By M. S. Armstrong

Attorney

Reissued Dec. 27, 1927. Re. 16,836

UNITED STATES PATENT OFFICE.

HARVEY S. COOK, OF VALPARAISO, INDIANA, ASSIGNOR TO COOK LABORATORIES, INC., OF CHICAGO, ILLINOIS, A CORPORATION OF DELAWARE.

HYPODERMIC SYRINGE.

Original No. 1,231,497, dated June 26, 1917, Serial No. 126,984, filed October 21, 1916. Application for reissue filed July 1, 1921. Serial No. 481,993.

This invention relates to syrjnges and particularly to hypodermic syringes and has for its object to provide a practicable and reliable instrument by which a physician may administer a hypodermic injection with convenience to himself and safety to the patient.

With this as the principal object in view, the invention consists in the novel construction, combination and arrangement of parts hereafter described and pointed out in the appended claims and illustrated in the accompanying drawing, in which:

Figure 1:
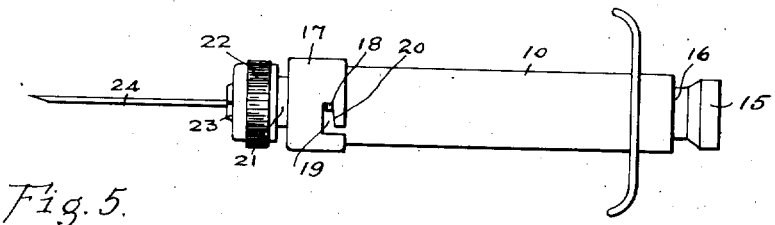
Figure 1 is a side elevation of the syringe.
Figure 5:
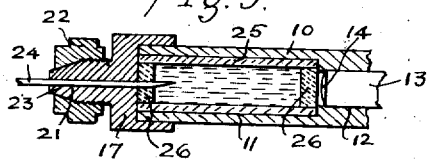
Fig. 5 is a longitudinal section showing the structure or organization of the instrument including its fluid medicament container.

In the drawings, 10 indicates a barrel or cylinder of the syringe, in one end of which and extending substantially one-half the length of the barrel is a chamber 11 for receiving a container of the solution to be injected, while the other half of the barrel has a bore 12 extending from the chamber 11 to the opposite end and of slightly less diameter than the chamber. Through the bore 12 slides a plunger 13 of a length sufficient to extend through the bore and into the chamber nearly to its opposite end when wholly depressed. The plunger 13 is cylindrical as shown and of the same diameter from its inner end 14 to its outer end which is provided with a button 15 to be grasped by the fingers for operating the plunger and has a shoulder 16 that forms a stop and abuts against the upper end of the barrel 10. The lower or outer end of the chamber 11 is closed by a cap 17 that fits snugly over the end of the barrel and is locked in place by pins 18 that project radially from the exterior of the barrel and engage slots 19 in the side of the cap, said slots having inclined walls 20 that, bearing against the pins 18 when the cap is rotated, lock said cap on the barrel.

Projecting axially from the cap is a threaded stem 21 on which a nut 22 is screwed, said nut serving as a coupling member for securely holding the clamping jaws 23 on the stem 21 and the needle 24 firmly in position. The needle 24 passes through an opening in the stem 21 and the cap 17 and may slide longitudinally therein whenever the nut 22 is unscrewed and the jaws 23 loosened, but as soon as the jaws are tightened on the needle, the latter becomes fixed and rigid with the cap and with the barrel 10.

The needle 24 is hollow as usual and the two ends pointed so that either end may be used for insertion beneath the skin.

A syringe constructed as described is quickly filled and easily cleaned owing to the fact that the cap and plunger may both be removed without trouble from the barrel. The plunger frame being cylindrical, being of equal diameter from end to end and without packing affords no means for lodgment of dirt thereon or the retention of the substance in the barrel. The chamber within the barrel is preferably straight from one end to the small shoulder where the bore begins and said bore is of the same diameter throughout its length. The needle is easily removed from the cap to enable the same to be cleaned or sterilized and the cap being preferably smooth on its inner side offers no corners for the lodgment of any unsanitary particles.

The liquid to be injected is carried in a container or ampul 25 made of glass in tubular form open at the ends and of a length to fit within the chamber 11. The ends of the container are closed and sealed by disks 26 of rubber, cork, or material that is readily perforated by the inner projecting end of the needle 24. In using the container, the cap 17 of the syringe is removed and the plunger withdrawn into the bore 12 after which the container is inserted in the chamber 11 and the cap 17 replaced, by which means the inner end of the needle punctures the closure 26 and projects into the container. Pressure on the plunger forces the upper closure through the container and the liquid therein through the needle.

Figure 2:
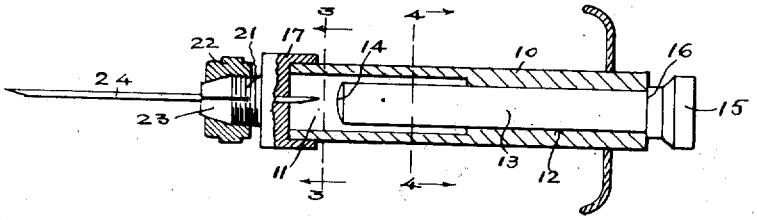
Fig. 2 is a longitudinal sectional view of the instrument without its fluid medicament container.
Figure 3:
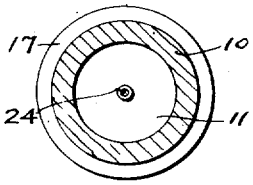
Fig. 3 is a cross sectional view on the line 3—3 of Fig. 2.
Figure 4:
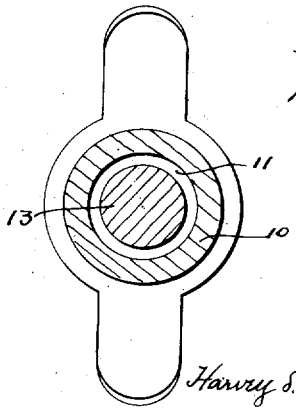
Fig. 4 is a similar view on the line 4—4, Figs. 3 and 4 being shown on a larger scale.

By using containers such as described, a great deal of time and trouble is saved as the contents of the containers are properly proportioned for injection and they contain the proper amount for an injection. A container comprising a straight glass tube of substantially uniform bore having sealing closures consisting of rubber or cork plugs in the opposite ends of the tube, is simple and practicable as a container for hypodermic medicament, and the sealing plug pierced by the inner end or extension of the hypodermic needle, being of resilient material such as rubber or the like, will closely hug the shank of the needle so as to prevent leakage or flow of fluid except through the needle, and will be self-sealing if the needle is withdrawn, so that there is no danger of contamination of the medicament fluid since there is no contact of the fluid with any part of the instrument excepting the sterilized needle. The resilient or yieldable material composing the sealing plugs also adapts them to conform to any slight irregularities in the inner bore of the tube to make effective sealing closures and enables the slidable plug at the end opposite to the needle to be forced through the tube without liability of cracking the glass. In the particular form shown, the sealing plugs or closures are duplicates, so that the container or ampul is reversible. The barrel constituting the holder for the medicament container or ampul, being properly proportioned to receive the same, has the hypodermic needle removably affixed to one end, so that the needle may be sterilized before assembly with the medicament container and has at its other end the plunger arranged and adapted to enter the glass tube to expel the fluid contents through the needle. The sealed ends of the medicament container seat in this instance against the head or cap 17 and the shoulder provided by the junction between the chamber 11 and the bore 12. Inward movement of the plunger is limited in this instance by the shoulder or stop 16, so that when the medicament is discharged and the plunger is in its extreme inward position, it is not likely to injure the point of the needle as will be apparent from Fig. 2.

What I claim is:

1. A syringe comprising a barrel having a straight cylindrical chamber extending thereinto from one end midway its length and a bore of less diameter extending from the chamber through to the opposite end, a cap containing a needle removably secured to the chamber end of the barrel, and a straight cylindrical plunger of uniform diameter fitted to the bore and of a length to extend therethrough and into the chamber when depressed.

2. A syringe comprising a straight cylindrical barrel having a chamber projecting thereinto at one end and extending midway its length, and a bore of less diameter extending from said chamber to the opposite end of the barrel, a cap movably fitted to the chambered end of the barrel and having projecting jaws, a needle extending through said cap and between the jaws and adapted to be rigidly secured by means of said jaws to the cap, and a straight cylindrical plunger of uniform diameter slidable through said bore and into the chamber.

3. A syringe comprising a barrel having a chamber in one end thereof extending midway its length and a straight cylindrical bore through its opposite end, the bore and the chamber communicating, a removable needle secured to the chambered end of the barrel, and a plunger of uniform diameter mounted in the bore to be pressed into the chamber and fill the same.

4. A syringe comprising a straight cylindrical barrel having a chamber formed in one end and extending miday the length thereof, and a bore of less diameter than the chamber extending from the chamber to the opposite end of the barrel, a straight cylindrical piston of uniform diameter slidable in said bore and into the chamber, pins projecting laterally from the outer surface of the barrel near the chambered end, a cap having locking slots adapted to fit on said barrel end and engage said pins by means of said slots for locking said cap in position, clamping jaws on the outer end of said cap, a needle passing through a perforation in the cap and between said jaws, and clamping means for operating the jaws to grip the needle.

5. A syringe comprising in combination, a barrel having a longitudinal chamber and a bore in communication with one end thereof; a removable needle secured to the other end of the barrel; a plunger in the bore constructed and arranged to be pressed into the chamber; and a removable, unitary medicament-dispensing container constructed and arranged to be inserted in the chamber to provide a charge of medicament for an injection; said container comprising a tube having sealing closures of resilient material at its opposite ends; one of said closures being adapted to be pierced to permit ejection of the medicament; the other closure being movable through the tube by means of the plunger, thereby dispensing the contents of the container without liability of contamination; each of said closures being of a material which is not injurious to the fluid medicament contained within the package, and at least one of the closures being so made that when pierced by a needle, it closes around the shank of the needle to prevent leakage or flow except through the needle, and after withdrawal of the needle is self-sealing to prevent contamination or loss of the medicament.

6. A syringe comprising, in combination, a barrel having a straight chamber open at one end, and a straight bore through its opposite end, the bore and the chamber communicating; a removable hollow needle secured at the open end of the barrel and extending therein; a plunger slidable through the bore and entering the chamber; and a combined medicament package and dispensing container constructed and arranged to be inserted in said chamber and comprising a tubular body; a resilient closure inserted in each end of the tubular body to seal it; the inner end of the needle piercing one closure; the plunger sliding the other closure through the tubular body toward the needle to dispense the contents through the needle; each of said closures being of a material which is quite resilient so that the closures accommodate themselves to tubes having small irregularities in internal bore, and which is not injurious to the fluid medicament contained within the package; and at least one of the closures being so made that when pierced by the needle, it closes around the shank of the needle to prevent leakage or flow except through the needle, and after withdrawal of the needle is self-sealing to prevent contamination or loss of the medicament.

7. A syringe comprising a barrel having a straight chamber in one end thereof extending midway its length and a straight cylindrical bore through its opposite end, the bore and the chamber communicating, a removable needle secured to the chambered end of the barrel, a plunger of uniform diameter mounted in the bore and adapted to be pressed into the chamber, and a removable container for the fluid to be injected of a size capable of being inserted in the chambered end of the syringe and having perforatable closures at its ends movable longitudinally in the container.

8. A hypodermic syringe comprising, in combination, a barrel; a removable hypodermic needle attached to one end of the barrel and having an inwardly protruding pointed extension in communication with the injecting point of the needle; a removable sealed container of fluid medicament mounted in the barrel, said container comprising a tube having an end sealing closure consisting of a plug of resilient material such as rubber or the like adapted to be readily pierced by said needle extension and to close around the same to prevent leakage or flow of fluid except through the needle and which will be self-sealing if the needle is withdrawn, said tube having an opposite end closure consisting of a plug adapted to be forced through the tube to expel the fluid contents through the needle; and a plunger associated with the barrel and arranged to enter said tube to force in said opposite plug.

9. A hypodermic syringe comprising, in combination, a sealed container of fluid medicament comprising a straight glass tube of substantially uniform bore having sealing plugs in its opposite ends; a barrel to receive said tube; a removable hypodermic needle attached to one end of the barrel and having a pointed extension in communication with the injecting point of the needle and which projects axially into the barrel to pierce the sealing plug at one end of said tube; the said plug being readily pierceable by said needle extension and consisting of resilient material such as rubber or the like which will close around said needle extension to prevent leakage or flow of fluid except through the needle and which will render the plug self-sealing if the needle extension is withdrawn; the opposite plug adapted to be pushed through said tube to expel the fluid contents through the needle; and a plunger associated with the barrel and arranged to enter said tube to push in said opposite plug.

10. A hypodermic syringe comprising, in combination, a barrel; a sealed container of fluid medicament therein comprising a straight glass tube of substantially uniform bore having sealing closures consisting of resilient plugs of rubber or the like secured in opposite ends of the tube; a removable hypodermic needle attached to one end of the barrel and having a pointed extension in communication with the injection point of the needle and which extends axially into the barrel to pierce the resilient plug at one end of the tube, said plug being readily pierceable thereby and the opposite plug adapted to be forced through the tube to expel the fluid contents through the needle; and a plunger associated with the barrel and arranged to enter said tube to force in said opposite plug.

11. A hypodermic syringe comprising, in combination, a sealed container of fluid medicament comprising a tube having an end sealing closure consisting of a resilient plug of rubber or the like adapted to be readily pierced by a hollow needle and to close around the same so as to prevent leakage or flow of fluid except through the needle and which will be self-sealing if the needle is wthdrawn, and having an opposite end closure consisting of a plug adapted to be forced through said tube to expel the fluid contents through the needle; and means associated therewith comprising a holder in which said tube is mounted having the said needle removably affixed thereto and arranged to pierce said first-mentioned plug and having a plunger adapted and arranged to enter said tube to force in the opposite plug.

12. A hypodermic syringe comprising, in combination, a sealed container of fluid medicament comprising a straight glass tube of substantially uniform bore having sealing plugs in its opposite ends, at least one of said plugs being readily pierceable by a hollow needle and consisting of resilient material such as rubber or the like which will close around the shank of the needle to prevent leakage or flow of fluid except through the needle and which will be self-sealing if the needle is withdrawn, and the other of which plugs is adapted to be forced through the tube to expel the fluid contents through the needle; and associated means comprising a holder in which said tube is mounted having the needle removably affixed thereto and arranged to pierce said first-mentioned plug and having a plunger adapted and arranged to enter said tube to force in the opposite plug.

13. A hypodermic syringe comprising, in combination, a sealed container of fluid medicament comprising a straight glass tube having sealing closures consisting of resilient plugs of rubber or the like secured in opposite ends of the tube; and associated means comprising a holder in which said tube is mounted having a removable needle arranged to pierce one of said plugs and having a plunger adapted and arranged to enter said tube to force the opposite plug therethrough to expel the fluid contents through the needle.

14. A hypodermic syringe comprising, in combination, a sealed medicament container having an end wall of resilient material adapted to be pierced by a hollow needle and to close around the same so as to prevent leakage or flow of fluid except through the needle and which will be self-sealing if the needle is withdrawn, said container constructed to have its interior volume reduced for expelling the fluid through the needle; and associated means comprising a holder in which the container is removably mounted having said needle removably attached thereto in position to pierce the said resilient end wall of the container and having means cooperative with the container for reducing its interior volume to expel its contents through the needle.

15. A hypodermic syringe cartridge comprising a sealed fluid-containing tube for use as a separable operative component of a syringe organization having a plunger at one end and an inwardly projecting needle at the other end, said tube having plugs in its opposite ends, including a plug of resilient material such as rubber or the like adapted to be pierced by the needle and which will seal around the needle and will be self-sealing if the needle is withdrawn, the other plug adapted to be pushed inwardly by the plunger to expel the fluid through such needle.

16. A hypodermic syringe comprising, in combination, a sealed medicament container, comprising a tube having an end sealing closure consisting of a plug of resilient material such as rubber or the like adapted to be pierced by a needle and to close around the same to prevent leakage or flow of fluid except through the needle, said tube having an opposite end closure consisting of a plug adapted to be forced through the tube to expel the fluid contents through the needle; associated means comprising a holder in which the container is removably mounted and having a plunger arranged to enter said tube to force in said opposite end closure for expelling the contents of the container through the needle; and a hollow needle in position to pierce the said resilient end wall of the container.

17. A hypodermic syringe comprising, in combination, a sealed medicament container having an end wall of resilient material adapted to be pierced by a hollow needle and to close around the same so as to prevent leakage or flow of fluid except through the needle; said container constructed to have its interior volume reduced for expelling the fluid through the needle; associated means comprising a holder in which the container is removably mounted, and having means cooperative with the container for reducing its interior volume to expel its contents through the needle; and a hollow needle in position to pierce the said resilient end wall of the container.

18. A hypodermic syringe cartridge comprising a sealed fluid-containing tube for use as an operative component of a syringe organization, said tube having plugs in its opposite ends, including an imperforate plug of resilient material such as rubber or the like adapted to be pierced by a needle and which will seal around the needle so as to prevent leakage or flow of fluid except through the needle, the other plug adapted to be pushed inwardly to expel the fluid through such needle.

In testimony whereof I affix my signature.

HARVEY S. COOK.